United States Patent [19]

Tanimizu et al.

[11] Patent Number: 5,439,646
[45] Date of Patent: Aug. 8, 1995

[54] BLOOD COAGULATION ANALYZER

[75] Inventors: Koji Tanimizu, Kyoto; Toshimi Kadota, Uji, both of Japan

[73] Assignee: Shimadzu Corporation, Kyoto, Japan

[21] Appl. No.: 121,375

[22] Filed: Sep. 15, 1993

[30] Foreign Application Priority Data

Sep. 30, 1992 [JP] Japan .................................. 4-286950

[51] Int. Cl.$^6$ ............................................. G01N 35/02
[52] U.S. Cl. ................................. 422/64; 422/63; 422/66; 422/67; 422/58; 422/82.05; 422/104; 436/43; 436/47; 436/48; 436/49; 436/165; 436/180
[58] Field of Search .................. 422/63, 64, 67, 168.1, 422/73, 66, 58, 82.05, 104; 436/43, 47, 48, 50, 54, 55, 49, 165, 180

[56] References Cited

U.S. PATENT DOCUMENTS

| | | |
|---|---|---|
| 4,234,539 | 11/1980 | Ginsberg et al. .................. 422/64 |
| 4,457,893 | 7/1984 | Takekawa ........................ 422/64 |
| 4,459,265 | 7/1984 | Berglund ........................ 422/64 |
| 4,647,432 | 3/1987 | Wakatake ........................ 422/64 |
| 4,785,407 | 11/1988 | Sakagami ........................ 364/497 |
| 4,835,707 | 5/1989 | Amano et al. .................... 364/497 |
| 4,896,963 | 1/1990 | Kato ............................. 356/328 |
| 5,051,238 | 9/1991 | Umetsu et al. ................... 422/64 |

Primary Examiner—James C. Housel
Assistant Examiner—Long V. Le
Attorney, Agent, or Firm—Klima & Hopkins

[57] ABSTRACT

A plurality of measuring modules are arranged on a table of a reaction part. The measuring module has one removable cell, and is provided with light sources and photodetectors. In proximity to the reaction part is a cell transfer part for mounting and dismounting the cell on and from the measuring module, a sampling probe for dispensing a sample into the cell, and a reagent probe for dispensing a prescribed reagent into the cell in response to a measurement item. A time from supply of each cell or dispensing of each sample to or in the reaction part to dispensing of a first reagent is controlled to be constant with no regard to the measurement items.

11 Claims, 5 Drawing Sheets

BLOOD COAGULATION ANALYZER

BACKGROUND OF THE INVENTION

1. Field of the Invention

The present invention relates to an analyzer for automatically analyzing blood coagulation in a clinical laboratory.

2. Description of the Background Art

In order to measure blood coagulation, a sample and a reagent are introduced into a cell, which in turn is moved to a coagulation measuring portion. In a general blood coagulation analyzer, such a measuring portion is provided with a photometer for irradiating the cell with a measuring beam emitted from a light source and detecting light scattered by a sample reaction solution with a photodetector.

In one of such conventional analyzers, a plurality of measuring portions are so provided that cells numbering the same as the measuring portions are successively transferred thereto for carrying out parallel processing, in order to improve processability for the blood coagulation analysis.

In another conventional blood coagulation analyzer, a cell containing a sample and at least one reagent can be selectively transferred to one of a plurality of measuring portions (refer to Japanese Patent Laying-Open Gazette No. 61-280572 (1986)).

However, coagulation times are varied with samples. In a conventional analyzer which successively transfers cells to fixed coagulation measuring portions, therefore, it is necessary to set a cycle time in response to a measurement item having the longest reaction time. Thus, it is difficult to improve processability of such an analyzer.

On the other hand, an analyzer which can selectively transfer a cell to any one of a plurality of measuring portions requires a complicated mechanism having a number of moving systems for moving every cell to a prescribed position in order to dispense a sample, dispense a reagent and mount/dismount the cell.

Further, reagent dispensation may be required once or twice, depending on the measurement items. For example, reagent dispensation may be carried out only once in PT (prothrombin time), FIB (fibrinogen), T(thrombo test) H (hepaplastin test), while actin must be previously dispensed as a reagent in APTT (activated part thromboplastin time) for activating a reaction solution of the reagent and the sample for a constant time, so that another reagent for serving as a trigger is thereafter dispensed. When sample dispensation or reagent dispensation is controlled in a random access manner, therefore, it may be necessary to dispense reagents in two cells during one cycle. Therefore, the aforementioned analyzer which can selectively transfer the cell to one of a plurality of measuring portions requires a complicated high-speed operation for successively transferring two cells to a single reagent dispensing position in a single cycle. Thus, the cycle time must be increased, to disadvantageously hinder improvement of processability.

SUMMARY OF THE INVENTION

A first object of the present invention is to simplify a mechanism for carrying out operations such as supply and discharge of cells, sample dispensation and reagent dispensation in a blood coagulation analyzer.

A second object of the present invention is to improve processability of a blood coagulation analyzer.

The present invention is directed to a blood coagulation analyzer comprising a reaction part which dismountably holds a plurality of cells, a supply/discharge mechanism for the cells, a sample dispenser and a reagent dispenser. The reaction part is provided with a plurality of measuring modules each of which has a measuring means for measuring coagulation of a sample solution contained in the cell and cell mounting position. The reaction part is also provided with a driving mechanism for moving and stopping the cell mounting positions of the measuring modules to and at a cell mounting/dismounting position, a sample dispensing position and a reagent dispensing position.

In the blood coagulation analyzer according to the present invention, a single operation cycle includes at least one of single cell supply operation, single sample supply operation, single cell discharge operation and single reagent dispensing operation, and a light measuring operation is carried out with these operations, while a time from cell supply or sample dispensation to or in the reaction part to dispensation of a first reagent is controlled to be constant with no regard to measurement items.

When it is predicted from timing of cell supply to the reaction part or sample dispensation to the cell that timing for dispensing a first reagent to the sample is overlapped with that for dispensing a second reagent to another cell to which sample dispensation has carried out, the operations are so controlled that the timing for the sample dispensing is shifted by at least one cycle.

The reaction part is moved at timing required for cell supply/discharge, sample dispensation and reagent dispensation, so that a prescribed measuring module is stopped at the position of a cell supply/discharge mechanism, the sample dispenser or the reagent dispenser.

According to the present invention, each of the cell supply/discharge mechanism, the sample dispenser and the reagent dispenser may operate only at a specific position of the reaction part, whereby the movement of each part is so simplified that the overall mechanism is simplified.

In the reaction part having the measuring modules which are provided for the respective cells, parallel processing of measurement is enabled in a plurality of measuring modules, thereby improving processability.

Further, the time from cell supply or sample dispensation to dispensation of the first reagent is so controlled to be constant that the cycle of cell supply or sample dispensation may be shifted only in analysis of measurement items requiring a second reagent and all measuring modules continuously operate in other case, whereby the analyzer can be efficiently driven with no waste time.

In addition, there is no need to repeat the same operation such as reagent dispensation in a single cycle, whereby the cycle time can be reduced to improve the processability also in this point.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
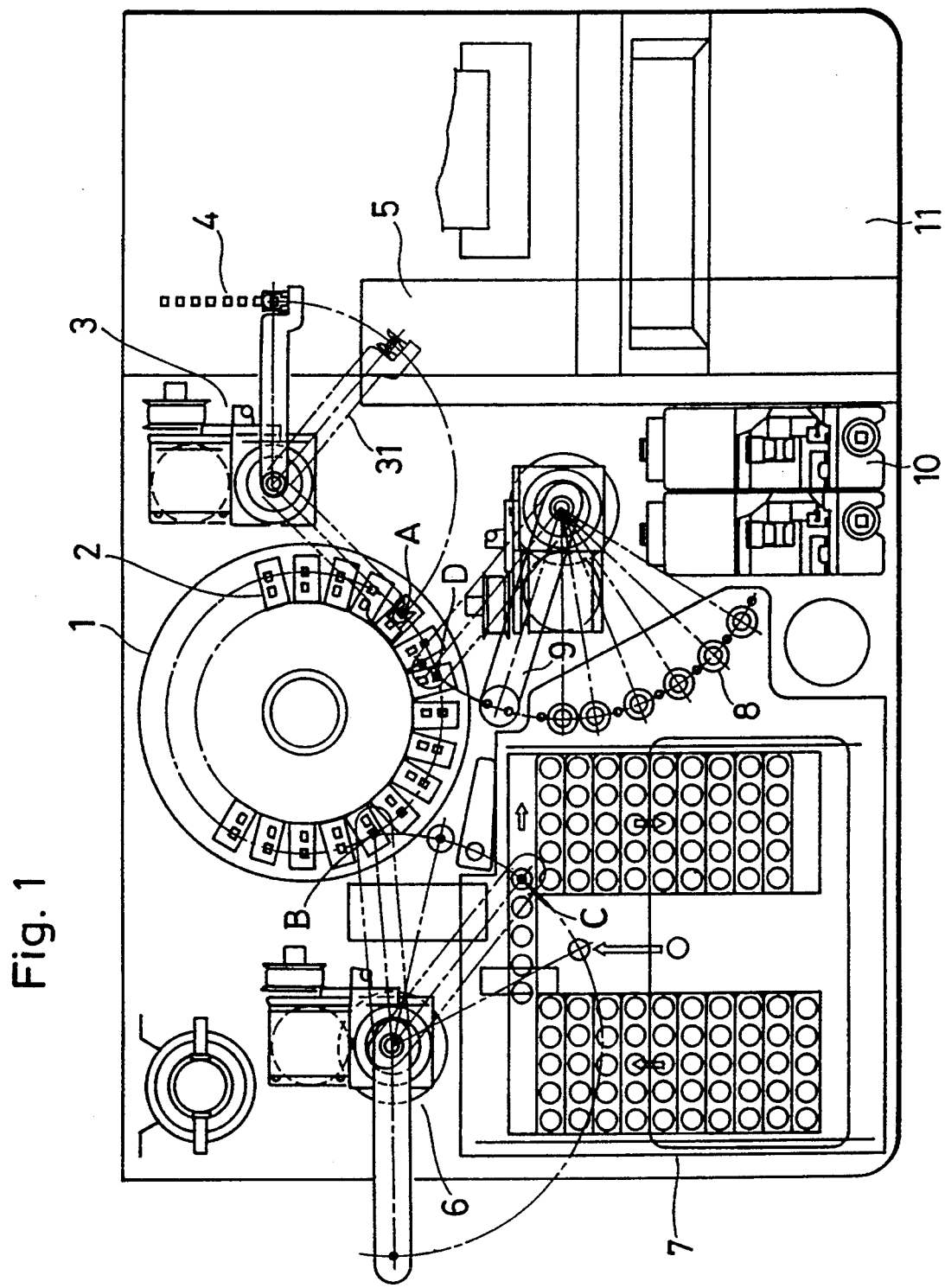
FIG. 1 is a plan view showing a blood coagulation analyzer according to an embodiment of the present invention.

FIG. 1 shows a blood coagulation analyzer according to an embodiment of the present invention. Referring to FIG. 1, a reaction part 1 has a discoidal table, which can be reciprocally rotated and stopped by a driving mechanism (not shown). A plurality of measuring modules 2 are arranged at regular intervals on the circumference of this table.

Figure 2:
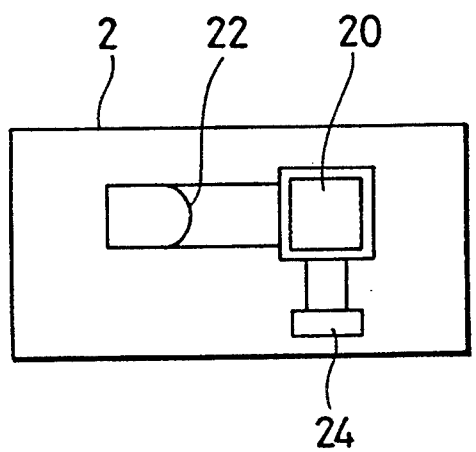
FIG. 2 is a plan view showing each measuring module in this embodiment.

As shown in FIG. 2, each measuring module 2 dismountably holds a cell 20 into which a sample and at least one reagent are dispensed. The measuring module 2 comprises a light source 22 such as an LED(Light Emission Diode) for irradiating a sample solution contained in the cell 20 with a measuring beam, and a photodetector 24 such as a photodiode provided on an optical axis which is perpendicular to the direction of incidence of the measuring beam for measuring light scattered from the measuring beam by the sample solution.

Referring again to FIG. 1, a cell transfer part 3 of a cell supply/discharge mechanism is provided in the vicinity of the reaction part 1, and a pivoting arm 31 is provided in this cell transfer part 3 for mounting each cell on each measuring module 2 and removing the cell from the measuring module 2 at a cell mounting/dismounting position A on the circumference of the table forming the reaction part 1. The arm 31, which has a mechanism for grasping and removing each cell on its forward end, is rotatably supported at its base end portion so that its forward end swings in an arcuate manner. In addition to the position A, the arm 31 is moved to and stopped at a position for receiving each cell from a cell supply part 4 and a position for disposing each cell to a cell disposal part 5. The cell supply part 4 has a mechanism for supplying each cell to the position for the arm 31 for grasping the same, while the cell disposal part 5 has a container for receiving each cell discharged from the arm 31. The cell transfer part 3 extracts the cells one by one from the cell supply part 4 to transfer and mount each cell toward and on each measuring module which is located on the position A of the reaction part 1, as well as to extract the as-measured each cell from the position A of the reaction part 1 for disposing the same in the cell disposal part 5. Although the cell transfer part 3 has two functions for supplying and disposing the cells according to this embodiment, such supply and discharge of the cells may alternatively be implemented by respective mechanisms.

A sampling probe 6 of a sample dispenser is provided in the vicinity of the reaction part 1, to aspirate each sample which is transferred to a position C of a rack-type sample transfer part 7 and dispense the sample in each cell of each measuring module which is located on a sample dispensing position B of the reaction part 1.

The sample transfer part 7 has an information reader (not shown) such as a bar code reader, while information for identifying each sample is provided on a sample vessel with a bar code or the like. The information reader reads such identification information from a sample vessel for a subsequently dispensed sample, to recognize a measurement item.

A reagent probe 9 of a reagent dispenser is further provided in the vicinity of the reaction part 1, to aspirate a prescribed one selected from a plurality of reagents 8 in response to the measurement item and dispense the same in each cell of each measuring module which is located on a position D of the reaction part 1.

Two syringe pumps 10 are connected with the sampling probe 6 and the reagent probe 9 through pipes respectively, to aspirate and discharge prescribed amounts of the sample and the reagent respectively. An operation part 11 includes a keyboard, a CRT, a printer and the like.

The blood coagulation analyzer according to this embodiment is provided therein with a control part for controlling operations of the respective parts. The operations controlled by the control part are now described.

Figure 3:
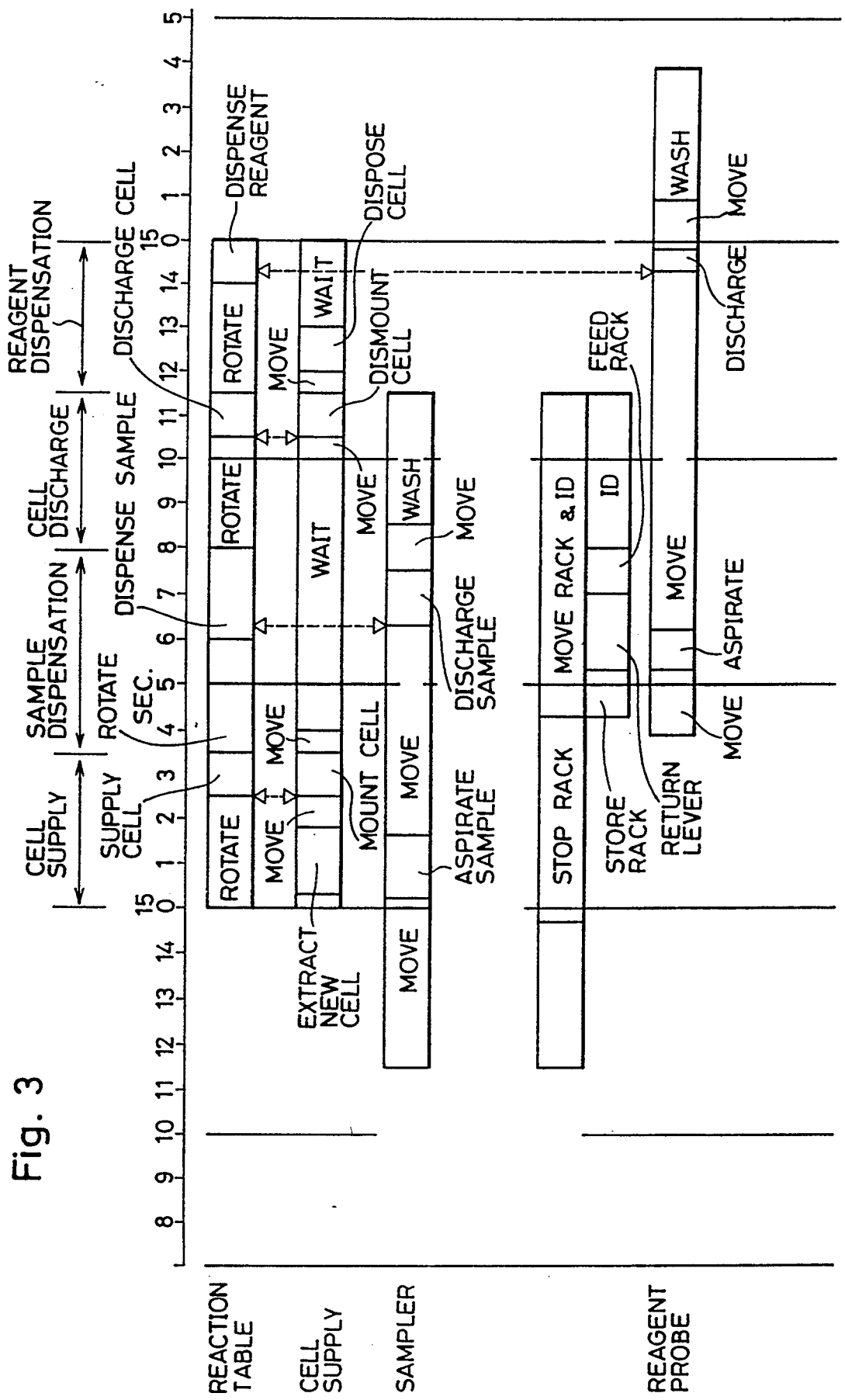
FIG. 3 illustrates an exemplary cycle of operations.

FIG. 3 illustrates the operations of the table of the reaction part 1, the cell transfer part 3, the sampling probe 6 and the reagent probe 9, with each cycle being formed by 15 seconds. A single cell supply operation, a single sample dispensing operation, a single cell discharge operation and a single reagent dispensing operation are allotted to each cycle.

In the sample transfer part 7, the information reader such as a bar code reader reads identification information, such as a bar code, provided on a sample vessel for a subsequently dispensed sample, so that the sample is then transferred to the position C. In a "CELL SUPPLY" interval appearing in FIG. 3, the table of the reaction part 1 is so rotated as to move a vacant measuring module 2 to the position A, and the cell transfer part 3 supplies a new cell to the measuring module 2 located on the position A. A prescribed amount of a sample which is located on the rack position C is aspirated by the sampling probe 6, to be transferred to the table position B.

In a "SAMPLE DISPENSATION" interval, the table of the reaction part 1 is so rotated that the measuring module 2 supplied with the cell is transferred to the table position B, and the sample is discharged from the sampling probe (sampler) 6 at this position for dispensation.

In a "CELL DISCHARGE" interval, the table of the reaction part 1 is so rotated that the measuring module 2 having the cell for the as-measured sample is transferred to the position A of the reaction part 1 and the cell is discharged from the measuring module 2 to the cell disposal part 5 by the cell transfer part 3. In parallel with this, the sampling probe 6 is moved to a washing position to be washed therein. In parallel with the "SAMPLE DISPENSATION" and "CELL DISCHARGE", the rack is moved in the sample transfer part 7 so that the information reader such as a bar code reader reads identification information from a sample vessel for a subsequently dispensed sample to recognize the measurement item.

In a "REAGENT DISPENSATION" interval, the table of the reaction part 1 is so rotated that a cell of a measuring module 2 is transferred to the position D after a lapse of a constant time from cell supply or sample dispensation and a reagent 8 corresponding to the measurement item for the sample in the cell is selected and aspirated by the reagent probe 9, to be dispensed in the cell located on the position D of the table of the reaction part 1.

In a next cycle, another measuring module 2 is employed to start measurement of another item in the same sequence as the aforementioned cycle.

Upon dispensation of the reagent, measurement of a coagulation process is started in the measuring module 2 and continued until the coagulation is completed, regardless of the operations of cell supply and discharge, sample dispensation and reagent dispensation.

Figure 4:
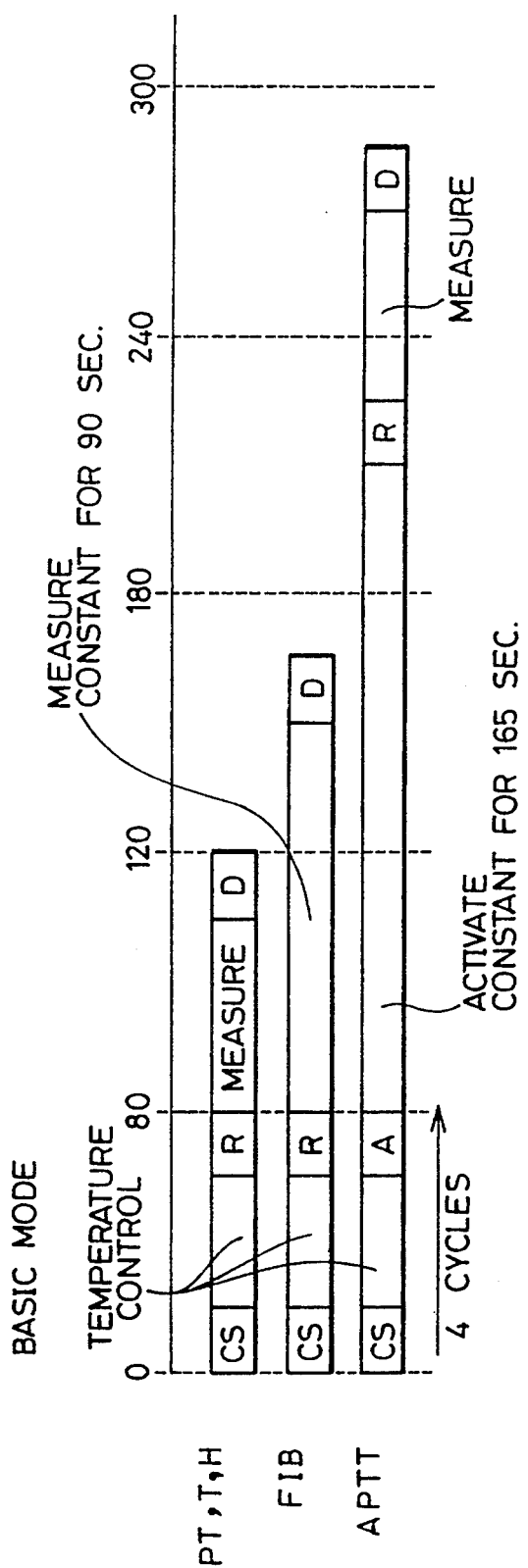
FIG. 4 illustrates exemplary basic modes of measurement items.

FIG. 4 shows basic modes of operations of respective items.

Reagent dispensation may be carried only once or must be carried out twice, depending on measurement items. For example, reagent dispensation may be carried out only once in PT, FIB and T/H, while actin is previously dispensed and activated for a constant time so that another reagent for serving as a trigger is thereafter dispensed in APTT. Referring to FIG. 4, symbols C, S, A, R and D represent cell supply, sample dispensation, APTT actin dispensation, reagent dispensation and cell discharge respectively.

This analyzer carries out the same operations in PT and T/H. Namely, each cell is supplied in a first cycle so that each sample is dispensed in the cell. After keeping at a constant temperature for two cycles, a reagent for serving as a trigger is dispensed in a fourth cycle as a first reagent. Measurement is started after such reagent dispensation, so that this measurement is completed and the cell is discharged upon detection of blood coagulation.

Also in FIB, cell supply and sample dispensation are carried out in a first cycle, and a reagent for serving as a trigger is dispensed as a first reagent in a fourth cycle after keeping at a constant temperature for two cycles. In this case, however, a measurement time is set constant for 90 seconds after the reagent dispensation, so that each cell is discharged after a lapse of 90 seconds.

Also in APTT, cell supply and sample dispensation are carried out in a first cycle, and a thermal keeping time is provided for two cycles. In this case, however, actin is dispensed in a fourth cycle as a first reagent. A time for 165 seconds is provided after the actin dispensation, and then a reagent for serving as a trigger is dispensed as a second reagent, to start measurement. Each cell is discharged after detection of blood coagulation.

FIG. 4 is characterized in that a time to dispensation of the first reagent is made constant regardless of the measurement items so that the first reagent is dispensed in a fourth cycle through two cycles from the first cycle including cell supply and sample dispensation.

Figures 5A, 5B:
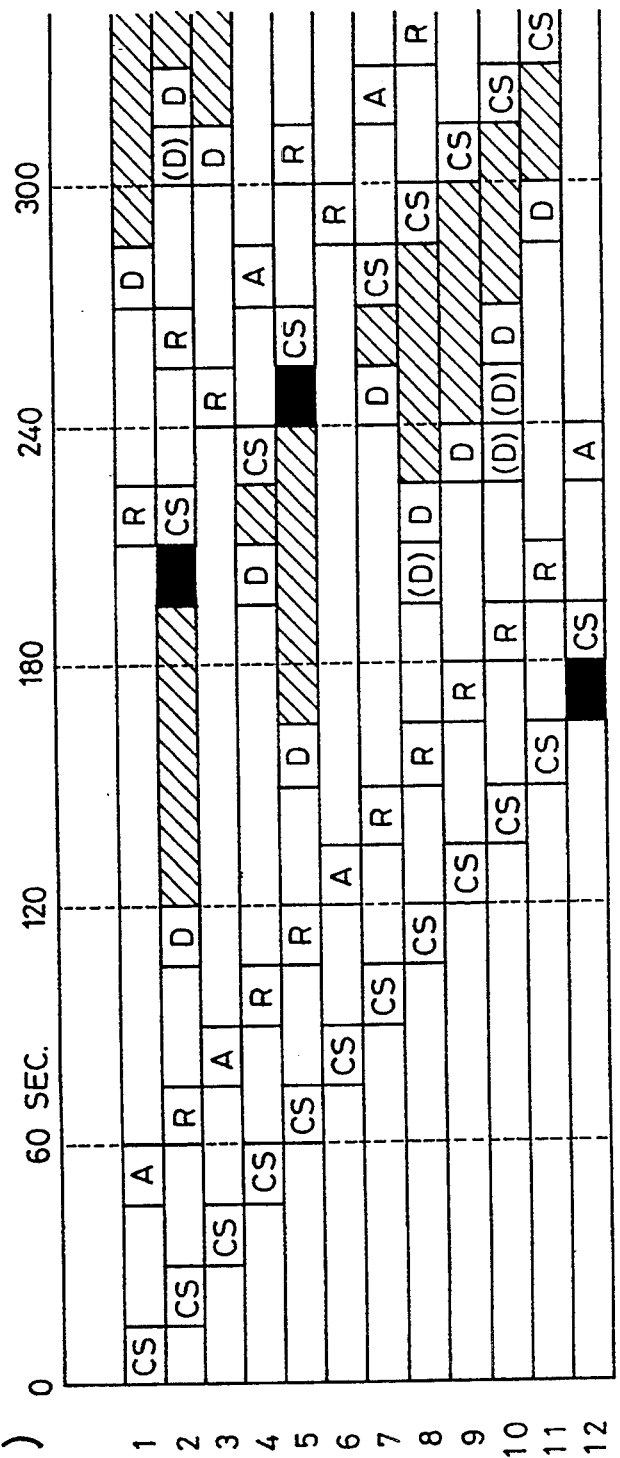
FIG. 5 illustrates overall operations in the embodiment.

FIG. 5 illustrates exemplary overall operations. Referring to FIG. 5, 12 measuring modules are employed for carrying out analysis. As shown in FIG. 4, the first reagent is dispensed after a lapse of a constant time from cell supply or sample dispensation. Referring to FIG. 5, each filled-up portion means that cell supply is shifted by one cycle from sample dispensation in a certain sample if timing of first reagent dispensation into this sample may be overlapped with that of second reagent dispensation in another sample being subjected to APTT measurement in the same cycle. This, the timing is so controlled as to cause no requirement for carrying out reagent dispensation twice in each cycle.

Timing for discharging each cell upon completion of measurement is also controlled to be shifted by at least one cycle to cause no requirement for discharging different cells at the same timing, as shown by symbols (D) in FIG. 5.

Table appearing in a lower portion of FIG. 5 shows measurement items of samples and as-employed cell numbers in correspondence to the upper Table. No measurement items are allotted to cycles in which cell supply and sample dispensation are shifted.

While the sample transfer part 7 is of a rack system in the embodiment shown in FIG. 1, this part may alternatively be formed by a turntable system one. Further, while the reaction part 1 is formed by a turntable system one in FIG. 1, this part may alternatively be formed by measuring modules which are connected with each other through a chain to carry out linear movement, or by other system of movement of measuring parts.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A blood coagulation analyzer, comprising:
    a reaction part comprising a plurality of movable measuring modules with each module having a removable cell and measuring means for measuring coagulation of a sample solution contained in said cell;
    a cell supply/discharge mechanism for supplying and discharging each cell to and from said measuring modules at a cell mounting/dismounting position of said reaction part;
    a sample dispenser for dispensing a sample into each said cell being located on a sample dispensing position of said reaction part;
    a reagent dispenser for dispensing a reagent into each said cell being located on a reagent dispensing position of said reaction part;
    a driving mechanism for moving and stopping each of said plurality of modules of said reaction part to and at said cell mounting/dismounting position, said sample dispensing position and said reagent dispensing position of said reaction part; and
    a control part for simultaneously measuring each of said cells in said plurality of modules.

2. A blood coagulation analyzer in accordance with claim 1, wherein said reaction part has a discoidal table being reciprocally rotatable and stoppable, said plurality of said measuring modules being arranged equal distances on a circumference of said table.

3. A blood coagulation analyzer in accordance with claim 2, wherein
    said measuring means comprises a light source for irradiating said sample solution with a measuring beam, and a photodetector being provided on an optical axis in a direction perpendicular to the incidence of said measuring beam for detecting light being scattered from said measuring beam by said sample solution.

4. A blood coagulation analyzer in accordance with claim 3, wherein
    said light source is an LED, and said photodetector is a photodiode.

5. A blood coagulation analyzer in accordance with claim 2, wherein said cell supply/discharge mechanism comprises a cell supply part for supplying each said cell to a prescribed position, a cell disposal part for receiving discharge from each said cell, and a pivoting mechanism having a mechanism for grasping and releasing each said cell located on a forward end portion and said pivoting mechanism is rotatably supported on a base end portion, said forward end portion of said mechanism being moved between said cell mounting/dismounting position on said table of said reaction part, a position for receiving each said cells in said cell supply part, and a position for discharging each said cell in said cell disposal part, and is arcuately stopped in each said position.

6. A blood coagulation analyzer in accordance with claim 1, wherein said sample dispenser comprises a sample transfer part for transferring a sample vessel to a position for aspirating each said sample, and a sampling probe for aspirating said sample from said sample vessel being transferred to said sample aspirating position by said sample transfer part and dispensing said sample into each said cell of each said measuring module being located on said sample dispensing position of said reaction part.

7. A blood coagulation analyzer in accordance with claim 6, wherein said sample transfer part has an information reader and said sample vessel is provided with identification information for identifying said sample, so that said information reader reads identification information of said sample to be subsequently dispensed, thereby recognizing a measurement item.

8. A blood coagulation analyzer in accordance with claim 1, wherein said reagent dispenser comprises a reagent probe for aspirating a reagent selected from a plurality of reagents in response to a measurement item and dispensing said aspirated reagent into each said cell of each said measuring module being located on said reagent dispensing position of said reaction part.

9. A blood coagulation analyzer, comprising:

a reaction part comprising a plurality of movable measuring modules with each module having a removable cell and measuring means for measuring coagulation of a sample solution contained in said cell;

a cell supply/discharge mechanism for supplying and discharging each said cell to and from said measuring modules at a cell mounting/dismounting position of said reaction part;

a sample dispenser for dispensing a sample into each said cell being located on a sample dispensing position of said reaction part;

a reagent dispenser for dispensing a reagent into each said cell being located on a reagent dispensing position of said reaction part;

a driving mechanism of said reaction part for moving and stopping said cell to and at said cell mounting/dismounting position, said sample dispensing position and said reagent dispensing position of said reaction part; and a control part adapted to carry out control so that at least one of a single cell supply operation, single sample supply operation, single cell discharge operation, single reagent dispensing operation are included in a single cycle of operations, and so that a light measuring operation of one of said measuring modules is carried out in parallel with said operations of the remaining said measuring modules, and a time from timing of a cell supply or sample dispensation to or in said reaction part to dispensation of a first reagent is constant with no regard to measurement items with respect to each said cell.

10. A blood coagulation analyzer in accordance with claim 9, wherein said control part controls the timing for dispensing a certain sample is shifted by at least one cycle when it is predicted from timing of cell supply to said reaction part or sample dispensation to said cell that timing for dispensing said first reagent into said sample is overlapped with that for dispensing a second reagent into another cell already having received another sample.

11. A blood coagulation analyzer in accordance with claim 9, wherein said control part controls operations to shift timing for discharging each cell one at a time.

* * * * *